United States Patent
Perez

(10) Patent No.: US 7,824,371 B2
(45) Date of Patent: Nov. 2, 2010

(54) FINGERTIP-POSITIONED ARTERY STABILIZER

(76) Inventor: James Gerard Perez, 4084 Bonita Rd., Bonita, CA (US) 91902

(*) Notice: Subject to any disclaimer, the term of this patent is extended or adjusted under 35 U.S.C. 154(b) by 100 days.

(21) Appl. No.: 11/549,076

(22) Filed: Oct. 12, 2006

(65) Prior Publication Data
US 2008/0172000 A1    Jul. 17, 2008

(51) Int. Cl.
*A61M 5/00*    (2006.01)
(52) U.S. Cl. .................. 604/115; 604/116; 604/117
(58) Field of Classification Search ......... 604/115–117
See application file for complete search history.

(56) References Cited

U.S. PATENT DOCUMENTS

| | | | | |
|---|---|---|---|---|
| 4,679,274 A | * | 7/1987 | Friedman | .............. 15/167.1 |
| 5,415,647 A | * | 5/1995 | Pisarik | ............... 604/115 |
| 5,693,041 A | * | 12/1997 | Murphy-Chutorian | ......... 606/2 |
| 6,652,487 B1 | * | 11/2003 | Cook | .............. 604/115 |
| 7,303,576 B2 | * | 12/2007 | Peters | ............... 606/201 |

* cited by examiner

*Primary Examiner*—Nicholas D Lucchesi
*Assistant Examiner*—Rebecca E Eisenberg

(57) ABSTRACT

An artery stabilizer device, which is held in place by a technician over a targeted artery using just one or two fingertips of the technician's hand, is provided for stabilizing the artery while the user inserts the needle of a syringe into the artery. A pair of stabilizer fingers, which protrude from the bottom surface of a finger-hold platform, hold the artery in place while the needle is inserted into the artery distal the tips of the stabilizer fingers. In one embodiment, a gauze pad is attached beneath the finger-hold platform, allowing the user to quickly apply a dressing over the wound created by the needle puncture. Another embodiment provides a needle guide between extended stabilizer fingers for stabilizing the needle during the arterial puncture. Each embodiment creates an augmented pulse at the targeted needle insertion site, making it easier for the technician to palpate the pulse there. Arterial line insertions can also be facilitated using this invention.

2 Claims, 4 Drawing Sheets

FINGERTIP-POSITIONED ARTERY STABILIZER

BACKGROUND OF THE INVENTION

1. Field of Invention

This invention relates generally to blood vessel stabilizing devices, specifically to an artery stabilizer device which a technician holds in place over a targeted artery using a fingertip of the technician's hand, to prepare the artery for the insertion of a needle therein.

2. History of Technology

In order to insert a percutaneous needle into a targeted artery, a medical technician will often struggle with instability of the artery during the procedure; the artery may tend to move away from an incoming needle. A second problem is that the artery may be hard to locate. A third problem is that it is impossible to keep exposed fingers safely away from the puncture site. The present invention solves these problems.

The withdrawal of arterial blood from a patient is a common procedure in today's health care settings. Arterial blood gas, or "ABG" analysis serves to provide vital information concerning the respiratory status of the patient. Blood is drawn anaerobically from an artery such as the radial, brachial, femoral, or dorsalis pedis artery, via a percutaneous needle puncture. The preferred site is the radial artery. A blood specimen is collected for direct measurement of the partial pressures of carbon dioxide (PaCO2) and oxygen (PaO2), hydrogen ion activity (pH), total hemoglobin (Hbtotal), oxyhemoglobin saturation (HbO2), and the dyshemoglobins carboxyhemoglobin (COHb) and methemoglobin (MetHb). Sampling typically may only be performed by trained and certified health care personnel.

A modified Allen Test (collateral circulation test) should always be performed by a technician before the technician inserts a needle into a patient's radial artery. The Allen Test determines if blood is capable of flowing through the ulnar artery. The ulnar artery is the only other source of blood to the hand aside from the radial artery. A negative test result is indicative of inadequate collateral blood supply to the hand and requires the selection of another location as the site for arterial access.

To obtain an arterial blood sample, the technician will first determine the precise location in which to insert the needle of a syringe into the artery of the patient. Once an appropriate site is located, the needle is inserted by the technician into the selected artery until the artery is penetrated and the syringe's blood receptacle fills with sufficient blood. Then, the needle is removed from within the artery, the wound is dressed, and the needle is capped to prevent needle injuries. The arterial blood draw process is difficult and prone to errors, even when the technician has ample experience. Because of the traumatic nature of the procedure, and the large number of complications that may arise, it is important for the technician to try to obtain the arterial blood properly and effectively on the first attempt. Prior art has seriously failed to provide technicians with adequate means to obtain a successful arterial blood sample regularly on the first attempt.

An unrestrained artery may tend to move away from an incoming needle, particularly in older patients whose skin has lost elasticity. A loss of elasticity in the skin creates a loss of stability around the artery, which allows the artery to roll around under the surface of the skin. It is possible for a needle tip to push the artery away from its path, causing the technician to miss the targeted artery completely. The present invention solves this problem by providing an artery stabilizer to hold the artery in place.

Currently, the technician will press her or his finger over the anticipated arterial puncture site and then estimate where the artery lies under that finger; it is a rough estimate and the technician often miscalculates. Alternatively, the technician may place two fingers over the artery and attempt to hold the artery between the fingertips, inserting the needle between the two fingertips to penetrate the artery. This method has its limitations; the technician should have a tight pair of gloves, cannot have long finger nails, and will rely on bulky fingertips to pinpoint a relatively thin artery between them, and this technique is impossible to use on infants and small children. The present invention uses an artery stabilizer to hold the artery within two integrated stabilizer fingers at the base of the device, and it partially occludes the artery during use; this creates an augmented pulse at the site where the needle will enter the artery, simplifying palpation of the artery and vastly diminishing the labor involved in identifying where to insert the needle. The artery stabilizer further allows the technician to keep any of the technician's exposed extremities substantially away from the puncture site while inserting the needle into the targeted artery, thus improving safety.

Because of low blood pressure, a patient's pulse may be weak and hard to locate. It is sometimes necessary for the technician to perform an arterial puncture "blindly," merely stabbing the site where the technician considers the best option for obtaining arterial access. The present invention helps to create an augmented pulse that is palpable even in cases of low blood pressure.

Most ABG protocols allow a technician to try three consecutive needle insertions without removing the needle tip beyond the subcutaneous tissue. As the angle of insertion changes within the dermis, the needle slices through the tissue in its path, and may even lacerate the artery. Any change in the angle of needle insertion can inflict severe pain onto a conscious patient. The present invention improves the chances for a successful puncture on the first try, thus minimizing pain, effort, and time.

The present invention also aids the technician in placing the introducer needle of a catheter syringe directly into a targeted artery. Arterial catheters, also known as arterial lines, are installed for, among other things, monitoring the blood pressure of a patient and for patients who require frequent blood draws. Current methods for inserting such catheters suffer from the same difficulties as those in attempting an arterial puncture for blood withdrawal. Using the present invention, the technician operates the catheter syringe the same as a typical syringe, benefiting from the augmented pulse created by the pressure of the stabilizer fingers over the selected artery to install the catheter effectively.

PRIOR ART

The number of devices within the realm of prior art related specifically to artery stabilizer devices is currently very limited. One such device, described by Ayer, is an invention which presses two protrusions down on either side of a targeted portion of a radial artery in order to hold the artery in place and prevent the artery from moving away from an incoming needle. The Ayer device requires a band to be strapped around the wrist of the patient. This band may tend to occlude the ulnar artery and thus restrict vital collateral blood flow through the ulnar artery to the hand. If the radial artery becomes occluded during the blood draw procedure, complete absence of blood flow to the hand can result, causing tissue trauma or death within that extremity. The current invention does not require a band to be placed around the wrist; more advantageously, it is a small device which is held in place by the technician over the targeted artery, thereby eliminating the risk of impeding the collateral blood flow through the ulnar artery when the radial artery is targeted. Another benefit over the Ayer device is that the present invention may be used on any artery, not just the radial artery. Another limitation of the Ayer device is that the device maintains a constant pressure over the targeted artery. As a result, it is not possible to reduce that pressure when it is time to withdraw the needle from the puncture site; the augmented pulse pressure can cause increased blood spillage out of the wound when the needle is removed. The present invention allows the technician to release the pressure over the artery before removing the needle from the puncture site.

Several devices have been proposed for stabilizing a vein for venipuncture, but none of the devices provide proper support for arterial puncture.

For arterial puncture, the blood vessel stabilizer portion of the device should be relatively small to accommodate the limited space over the radial artery near the patient's hand, it should be shaped to facilitate palpation of the targeted puncture site by the technician, and it should be shaped to allow the insertion of a needle into the artery nearest the patient's heart relative to the stabilizer.

The device should be designed to allow a proper angle of needle passage into the artery, and it should be easily removed; it cannot be bound or taped down during use. These features are all present in the current invention. The present invention allows the technician to palpate the targeted puncture site with the same hand that holds the device down over the artery. The present invention may include an adjustable artery stabilizer to accommodate various sizes of targeted arteries.

OBJECTS AND ADVANTAGES

Several objects and advantages of the present invention include providing a fingertip-positioned artery stabilizer device that:

(a) holds a targeted artery in place for the insertion of a needle therein.

(b) isolates the artery and creates an augmented pulse for easy identification of the precise location of the artery.

(c) is held in place by the technician using only one hand.

(d) allows unrestricted blood flow through the ulnar artery.

(e) shields the technician's finger from the sharp needle tip during use, to prevent inadvertent injury.

(f) is inexpensive to manufacture, simple and intuitive to use, disposable, light-weight, and reusable if cleaned and disinfected properly.

(g) can be used on any individual of any age and size, and on any suitable artery.

(h) minimizes the need for multiple attempts to penetrate the artery.

(i) allows the technician to regulate the pressure of the device over the artery and to easily release the pressure before removing the needle from that artery.

(j) can be used for inserting a catheter into a targeted artery.

(k) can be applied over the targeted artery using one finger of one of the technician's hands, allowing another finger of the same hand to simultaneously apply pressure over that artery beyond the insertion site to stop the blood flow to the insertion site.

(l) can be used with a large variety of available syringes.

(m) allows the technician to alter the width between each artery stabilizer finger.

DETAILED DESCRIPTION OF THE INVENTION

Figure 1:
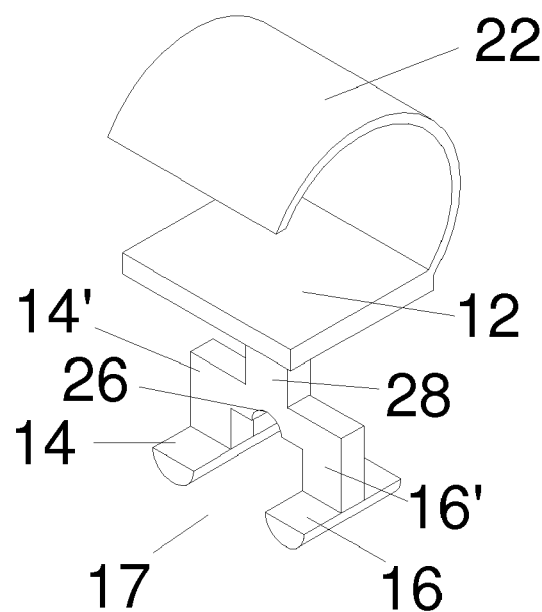
FIG. 1 is a perspective view of the invention.

Referring now to the drawings, FIGS. 1-7 represent various embodiments and designs of the present invention. Turning first to FIG. 1, artery stabilizer 10 is attached to platform 12. Stabilizer fingers 14 and 16 emanate from the bottom surface of platform 12. The technician presses the bottom surface of stabilizer fingers 14 and 16 over each side of a targeted artery before an arterial puncture attempt. The technician then palpates the targeted insertion site to verify proper placement, and then inserts the needle of a syringe or other needle-bearing device into the targeted artery between fingers 14 and 16, distal the tips of fingers 14 and 16. The tip of the needle would pass beneath platform 12, between extensions 14' and 16' of each stabilizer finger, and then through point 17 and into the targeted artery. Alternatively, only one finger protrudes beneath platform 12, and the single finger would hold only one side rather than both sides of a targeted artery. Grasping member 18 protrudes above platform 12 to give the technician something to grasp in order to more easily maneuver the device. The device can be removed from the work site prior to removing the needle from within the artery, thus freeing one of the technician's hands for dressing the wound created by the needle puncture. The invention is capable of being reused if it is cleaned and disinfected properly. It can be made of any durable solid material such as plastic or metal. It can be transparent or opaque.

Figure 2:
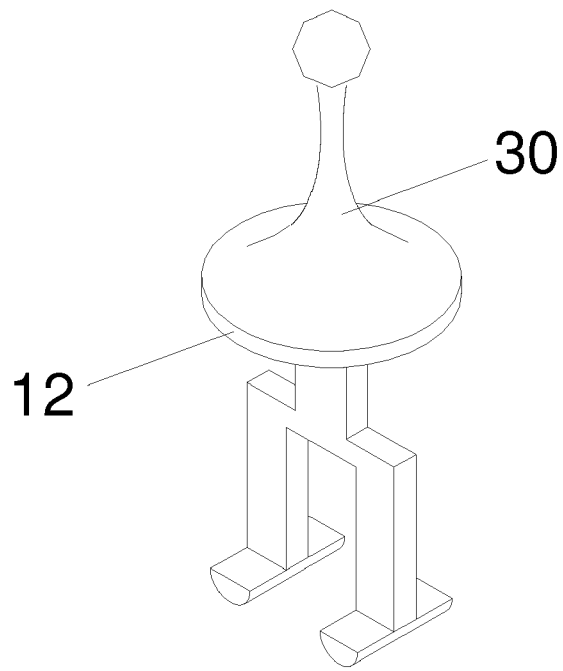
FIG. 2 is a perspective view of an alternative embodiment which utilizes a clip to hold the device on the fingertip of the technician's hand, and includes a needle guide.

Turning now to FIG. 2, clip 22 flexes to allow the technician to place one of the technician's fingers between platform 24 and clip 22, clip 22 thereby holding the device on the technician's fingertip. Needle guide 26 helps stabilize and position the needle of a syringe during a needle insertion procedure; the technician presses the shaft of the needle against needle guide 26 as the needle is moved toward or away from a targeted artery. Extension 28 lengthens the distance between platform 24 and the bottom surface of each stabilizer finger.

Figure 3:
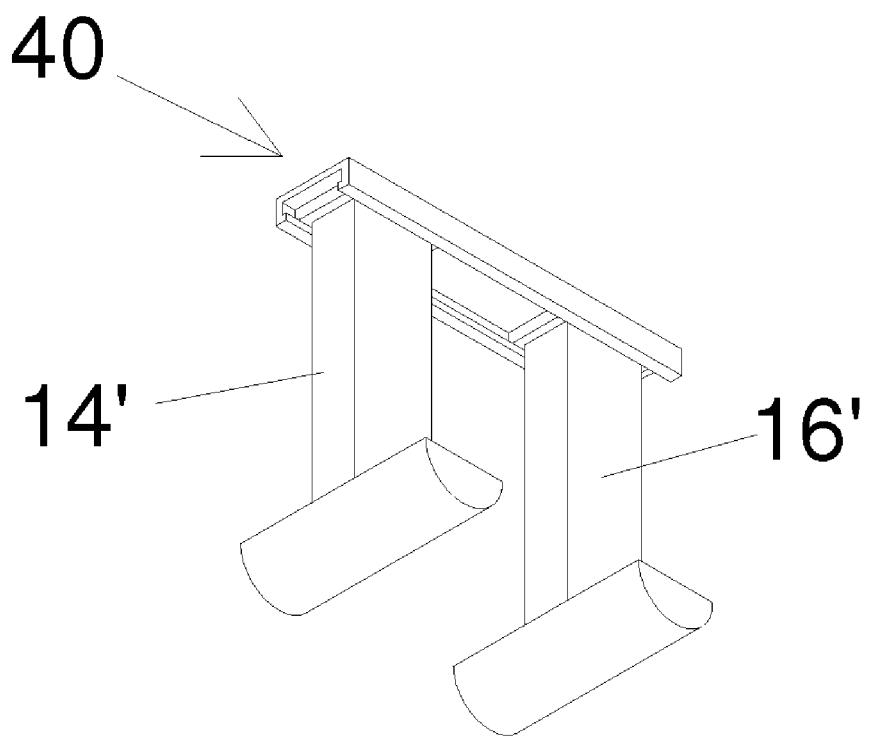
FIG. 3 is a perspective view of an alternative embodiment which utilizes a grasping member which helps the technician to wield the device.

Turning to FIG. 3, grasping member 30 has a different shape. The grasping member can be shaped and sized in a vast number of alternative ways.

Figure 4:
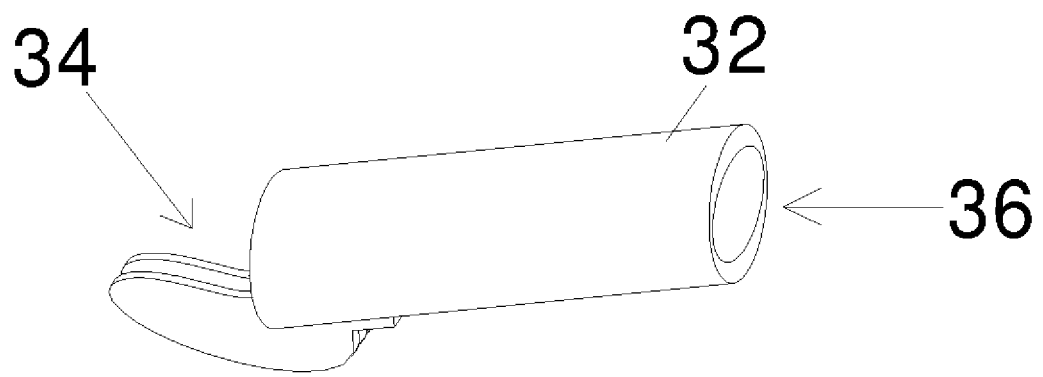
FIG. 4 is a perspective view of an alternative embodiment which utilizes a finger cot to hold the device on the fingertip of the technician's hand, and a needle is passed over the device rather than below the platform.

Referring to FIG. 4, an alternative embodiment utilizes finger cot 32 to hold artery stabilizer 34 on the finger of the technician. The technician places the finger in through opening 36. The cot may be made of pliable plastic, latex, or any other elastic or flexible material, preferably a hypoallergenic material.

Figure 5:
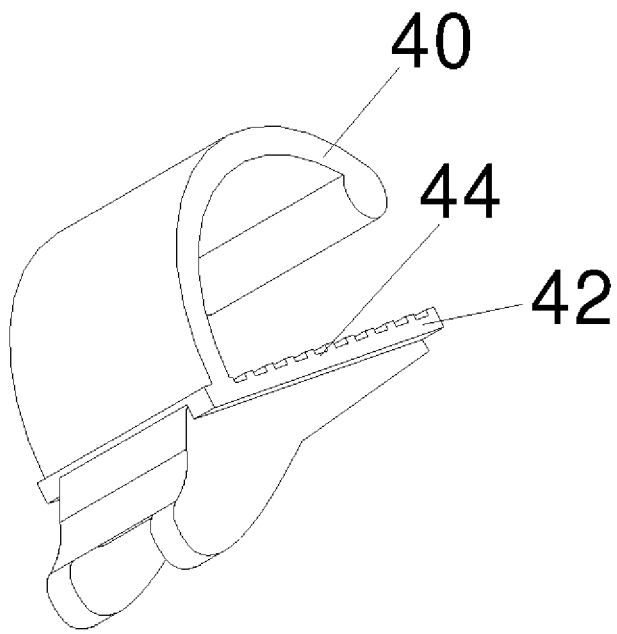
FIG. 5 is a perspective view of an alternative embodiment where the needle is passed over the device rather than below the platform.

Referring now to FIG. 5, clip 40 secures finger-hold platform 42 to the technician's finger. The technician's finger is held in place between flexible clip 40 and the top surface 44 of platform 42. Any finger may be used to support the device over the targeted artery, but the thumb or the index finger is recommended. By using the thumb, the technician can use the index or middle finger of the same hand to apply pressure over the artery distal the insertion site before the needle is retracted from within the artery, thus occluding the flow of blood through the artery and preventing blood from spilling out of the wound when the needle is removed from the puncture site. This gives the technician time to place a gauze dressing over the wound without encountering blood spillage. Another method is to release the pressure which the device exerts over the artery before the needle is removed from the artery, thereby bringing the augmenting pulse pressure back to normal. The technician can then remove the needle from the artery without encountering undue blood spillage just before applying a dressing over the puncture wound.

Figure 6:
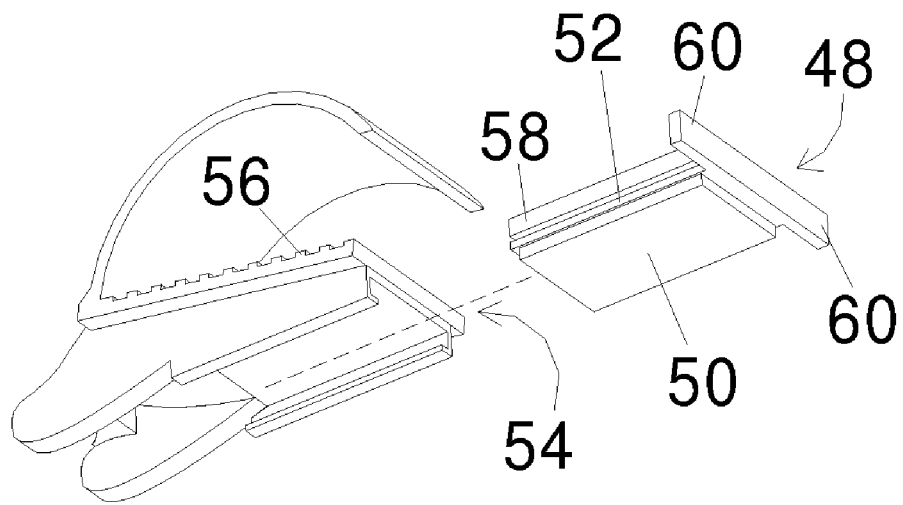
FIG. 6 is a perspective view of a gauze dressing member which can be detached from the device and secured over a wound.

Turning now to FIG. 6, gauze dressing member 48 includes gauze pad 50 which is attached to the bottom of gauze holder 52. Gauze dressing member 48 can be installed or removed from within gauze holder track 54 which is integrated beneath platform 56. Gauze holder edges 58 are shaped to slide into gauze track 54. After the needle insertion procedure, the technician can move gauze pad 50 over the wound to dress it. By retaining graspable tabs 60, the technician can slide the entire device off of dressing member 48, leaving just dressing member 48 over the wound. Dressing member 48 can be taped down over the wound.

Figure 7:
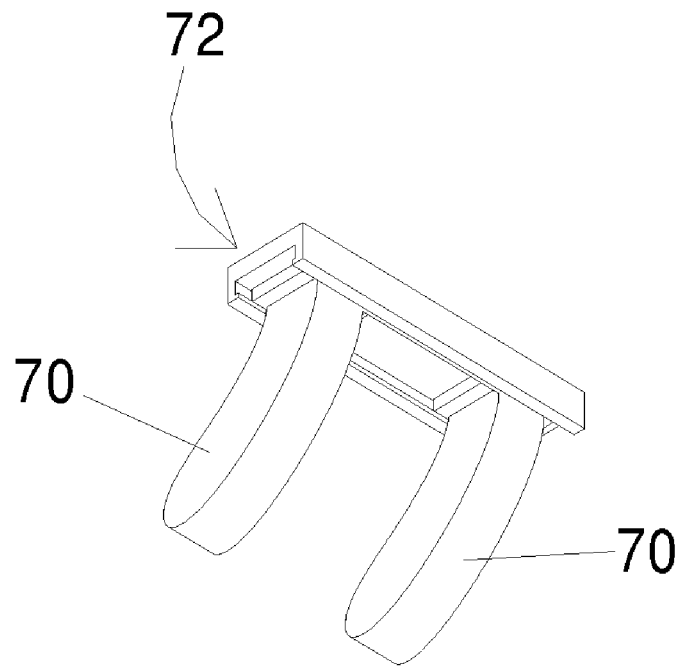
FIG. 7 is a perspective view of a track adapted to allow adjustability of the distance between each stabilizer finger

Turning finally to FIG. 7, extension members 14' and 16' are slidably situated within artery stabilizer adjustment track 40 so that the distance between each stabilizer finger can be altered to accommodate various sizes of targeted arteries. It can be designed as a more complex apparatus, such as one that requires the technician to turn a knob to alter the distance between each stabilizer finger, but a simple one is shown here for ease of illustration.

What is claimed is:

1. A fingertip-positioned artery stabilizer device comprising:

Two solid stabilizer fingers each comprising a length and a width, wherein said stabilizer fingers are configured to be placed over each side of a targeted artery before puncturing said artery; further comprising extensions and a platform said stabilizer fingers connected to said platform; wherein said extensions are further connected to a needle guide, said needle guide configured to stabilize and position the needle of a syringe during needle insertion; wherein a flexible clip member is attached to the platform and configured to allow a technician to hold the device on said technicians fingers.

2. A fingertip-positioned artery stabilizer device comprising:

Two solid stabilizer fingers each comprising a length and a width, wherein said stabilizer fingers are configured to be placed over each side of a targeted artery before puncturing said artery; further comprising extensions and a platform said stabilizer fingers connected to said platform; an adjustment track connected to the stabilizer fingers, where the adjustment track allows the distance between each stabilizer to be adjusted to accommodate various sizes of targeted arteries; wherein a flexible clip member is attached to the platform and configured to allow a technician to hold the device on said technicians fingers.

* * * * *